(12) United States Patent
Masuyama (10) Patent No.: US 8,613,916 B2
(45) Date of Patent: Dec. 24, 2013

(54) IMMUNOTHERAPY FOR PANCREATIC CANCER

(75) Inventor: Jun-ichi Masuyama, Oyama (JP)

(73) Assignee: Cellex Corporation, Tokyo (JP)

( * ) Notice: Subject to any disclaimer, the term of this patent is extended or adjusted under 35 U.S.C. 154(b) by 212 days.

(21) Appl. No.: 13/377,893

(22) PCT Filed: Oct. 6, 2009

(86) PCT No.: PCT/JP2009/005185
§ 371 (c)(1),
(2), (4) Date: Dec. 13, 2011

(87) PCT Pub. No.: WO2010/146634
PCT Pub. Date: Dec. 23, 2010

(65) Prior Publication Data
US 2012/0093792 A1    Apr. 19, 2012

(30) Foreign Application Priority Data
Jun. 19, 2009  (JP) ................. 2009-146739

(51) Int. Cl.
*A01N 63/00*    (2006.01)
(52) U.S. Cl.
USPC .......... 424/93.1; 435/325; 435/372; 435/373; 435/375; 530/350; 530/387.1; 530/388.7; 530/388.73
(58) Field of Classification Search
USPC ................... 424/93.1; 530/350, 387.1, 388.7, 530/388.73; 435/325, 372, 373, 375
See application file for complete search history.

(56) References Cited

FOREIGN PATENT DOCUMENTS

| | | |
|---|---|---|
| JP | 3056230 | 6/2000 |
| JP | 2002045174 | 2/2002 |
| JP | 2005124568 | 5/2005 |
| JP | 2006340698 | 12/2006 |
| JP | 3951350 | 8/2007 |
| JP | 2007297339 | 11/2007 |
| WO | 2008035461 | 3/2008 |
| WO | 2008081927 | 7/2008 |

OTHER PUBLICATIONS

Yamaue et al. (Nihon Gan Chiryo Gakkai Shi. May 20, 1990; 25 (5): 978-89).*
Nagler et al. (Bone Marrow Transplant. Oct. 1997; 20 (7): 525-31).*
Sussman et al. (Ann. Surg. Oncol. Jul. 1994; 1 (4): 296-306).*
Yamaguchi et al. (Hum. Cell. Dec. 2003; 16 (4): 183-9).*
Hirooka et al. (Pancreas. Apr. 2009; 38 (3): e69-74).*
Lygidakis et al. (Hepatogastroenterology. Dec. 1993; 40 (6): 574-81).*
Peiper, M. et al., Human pancreatic caner cells (MPanc-96) recognized by autologous tumor-infiltrating lymphocytes after in vitro as well as in vivo tumor expansion, Int J Cancer, 1997, vol. 71, No. 6, p. 993-999.

* cited by examiner

*Primary Examiner* — Stephen Rawlings
(74) *Attorney, Agent, or Firm* — Berenato & White, LLC

(57) ABSTRACT

The present invention provides an immunotherapeutic agent and immunotherapy allowing the extension of the survival time of patients with pancreatic cancer. The immunotherapy of the present invention is characterized by comprising the steps of culturing peripheral blood lymphocytes of a patient with pancreatic cancer by stimulating the lymphocytes with an anti-CD3 antibody and an anti-CD52 antibody, thereby to obtain an immunotherapeutic agent, and administering at least four infusions of the resultant immunotherapeutic agent to the same patient, wherein each of the infusions of the immunotherapeutic agent comprises at least $15 \times 10^9$ cells of activated lymphocytes, the percentage of $CD3^-$ $CD56^+$ NK cells in the activated lymphocytes is at least 30%, and the administration of the immunotherapeutic agent is begun for the patient who is in at least one state of two or more particular immunocompromised states.

4 Claims, 8 Drawing Sheets

Fig. 8

IMMUNOTHERAPY FOR PANCREATIC CANCER

CROSS-REFERENCE TO RELATED APPLICATION AND CLAIM TO PRIORITY

This application is a national stage application of PCT/JP2009/005185, filed on Oct. 6, 2009 which claims priority to JP 2009-146739, filed on Jun. 19, 2009, the disclosures of which are incorporated herein by reference and to which priority is claimed.

BACKGROUND OF THE INVENTION

1. Field of the Invention

The present invention relates to an immunotherapy for patients with pancreatic cancer, employing an immunotherapeutic agent. The immunotherapeutic agent of the present invention comprises, as the main constituent, activated lymphocytes cultured from peripheral blood lymphocytes of the patients, wherein the activated lymphocytes contain high percentages of $CD3^-$ $CD56^+$ NK cells.

2. Description of the Related Art

There are known immunotherapies for various types of cancers. In adoptive immunotherapies in particular, for instance, peripheral blood lymphocytes derived from a patient with cancer are activated with an antibody or antibodies, and expanded during culture, and then administered to the same patient, as an immunotherapeutic agent in a sense. The activated lymphocytes have various immunological functions. Among the activated lymphocytes are T and natural killer (NK) cells having cytotoxic activities against tumor cells.

NK cells are large granular lymphocytes which account for 10 to 20% of the human peripheral blood lymphocytes. Activated NK cells have non-specific cytotoxic activity or antibody-dependent cell-mediated cytotoxicity (ADCC) against tumor cells, virus-infected cells, and the like. Different from T and B cells which develop into memory cells following the sensitization with antigens, such sensitization is not required for NK cells to attack tumor cells. Generally, NK cells attack tumor cells in a molecule-specific way immediately when directed to cancer cells. On the surface of activated NK cells, surface receptors inducing cytotoxic effects on tumor cells are expressed, such as NKG2D, TRAIL (TNF Related Apoptosis Inducing Ligand), and others.

Japanese Patent No. 3056230, Japanese Unexamined Patent Publication (Kokai) No. 2002-45174, Japanese Unexamined Patent Publication No. 2006-340698 and Japanese Patent No. 3951350 disclose culture methods by which various types of cells contained in the peripheral blood lymphocytes are selectively propagated. Japanese Patent No. 3056230, Japanese Unexamined Patent Publication (Kokai) No. 2002-45174 and Japanese Unexamined Patent Publication No. 2006-340698 relate to methods by which NK cells are propagated at relatively high percentages. Japanese Patent No. 3951350 relates to methods by which NK cells obtained are present at extremely small percentages or are hardly contained.

RELATED REFERENCES

Patent reference 1. Japanese Patent No. 3056230
Patent reference 2. Japanese Laid-open Publication No. 2002-45174
Patent reference 3. Japanese Laid-open Publication No. 2006-340698
Patent reference 4. Japanese Patent no. 3951350
Non-patent reference 1. Heinemann V, et al. BMC Cancer 2008, 8:82
Non-patent reference 2. Tanaka T, et al. Jpn J Clin Oncol 2008, 38:755
Non-patent reference 3. Okusaka T, et al. Cancer Chemother Pharmacol 2008, 61:615
Non-patent reference 4. Strumberg D, et al. 2009 Gastrointestinal Cancers Symposium, Abstract#195
Non-patent reference 5. Nakamura K, et al. Br J Cancer 2006, 94:1575
Non-patent reference 6. Ueno H, et al. 2007 ASCO, Abstract#4550
Non-patent reference 7. Lee G, et al. 2008 ASCO, Abstract#15577
Non-patent reference 8. Kim M Y, et al. Jpn J Clin Oncol 2009, 39:49

Japanese Patent No. 305623 describes immunotherapies of three cases employing cultured activated lymphocytes. These immunotherapies were directed against malignant melanomas or liver cancers. In Japanese Unexamined Patent Publication (Kokai) No. 2002-45174, cytotoxic activities on tumor cells were measured employing proliferation-stimulating antibodies used during the culture. In Japanese Unexamined Patent Publication (Kokai) No. 2002-45174, however, no examples applied actually to cancer patients were described. Immunotherapies for various types of cancers also include methods in which lymphocytes consisting predominantly of T cells and others are employed (Japanese Patent No. 3951350), apart from methods in which lymphocytes consisting predominantly of NK cells are employed.

However, no immunotherapy has been presented which is effective against pancreatic cancer. In pancreatic cancer, due to the structure of the pancreas, cancer cells developed from epithelial cells of the organ are prone to infiltrate into surrounding tissues and metastasis in the whole body. Therefore, a cancer lesion has often become an already advanced cancer at the time when the diagnosis of pancreatic cancer has been made. As a result, cases with pancreatic cancer to which resection is applicable are limited, in as small a number as 20 percent or so, and the post-operative survival rate is also low, compared to cancers of the stomach, colon and others. In this connection, Heinemann, V. et al., BMC Cancer, 2008, 8:82; Tanaka, T. et al., Jpn J Clin Oncol, 2008, 38:755; Okusaka, T. et al., Cancer Chemother Pharmacol, 2008, 61:615; Strumberg, D. et al., 2009 Gastrointestinal Cancers Symposium, Abstract #195; Nakamura, K. et al., Br J Cancer, 2006, 94:1575; Ueno, H. et al., 2007 ASCO, Abstract #4550; Lee, G. et al., 2008 ASCO, Abstract #15577; and Kim, M. Y. et al., Jpn J Clin Oncol, 2009, 39:49 report survival rates at one year after diagnosis in pancreatic cancer patients who were treated with anti-cancer agents alone. The patients' survival rates were mostly in the range of 15 to 33%, except that the survival rate in Nakamura, K. et al., Br J Cancer, 2006, 94:1575 was 54%. Thus, pancreatic cancer is a typical carcinoma having a very poor prognosis.

As mentioned above, pancreatic cancer is a rapidly progressive disease. Even if immunotherapies are effective for cancers other than pancreatic cancer, it is unclear whether or not such immunotherapies are useful for pancreatic cancer. An object of the present invention is to provide an immunotherapy effective against pancreatic cancer.

SUMMARY OF THE INVENTION

The immunotherapy for pancreatic cancer according to the present invention comprises the following steps:1) the immunotherapeutic agent of the present invention is obtained by stimulating peripheral blood lymphocytes derived from a patient with pancreatic cancer using an anti-CD3 antibody and an anti-CD52 antibody followed by culturing, 2) the immunotherapeutic agent is administered at least four times to the same patient, 3)each of the infusions comprises at least $15 \times 10^9$ activated lymphocytes, 4) the activated lymphocytes consist of at least 30% $CD3^- CD56^+$ NK cells, 5) further, the immunotherapeutic agent is administered to patients who fulfills at least one of the following immunocompromised states:
(a) the number of peripheral blood lymphocytes being less than 1,000 cells/μl;
(b) the number of $CD3^- CD56^+$ NK cells in the peripheral blood lymphocytes being less than 200 cells/μl;
(c) thecytotoxic activity of $CD3^- CD56^+$ NK cells in the peripheral blood lymphocytes being less than 30%; and
(d) the number of $NKG2D^+$ lymphocytes in the peripheral blood being less than 400 cells/μl.

Further, it is preferable that the immunotherapeutic agent of the present invention is administered to patients with pancreatic cancer having the $CD4^+$ T cells/$CD8^+$ T cells (CD4/CD8) ratios of more than 3 in peripheral blood lymphocytes.

It is also preferable that the administered activated lymphocytes other than NK cells are either or both of $CD4^+$ T cells and $CD8^+$ T cells.

It is also preferable that the immunotherapeutic agent is administered in combination with anti-cancer agents.

The present inventors have presented, in Japanese Unexamined Patent Publication No. 2006-340698, culture techniques for mass propagating of $CD16^+$ NK cells from peripheral blood of 30 ml or so. $CD16^+$ NK cells are the same as $CD3^- CD56^+$ NK cells. An immunotherapeutic agent for use in the immunotherapy of the present invention comprises, as the main constituent, activated lymphocytes which are obtained by mass culture methods based on these culture techniques. The activated lymphocytes comprise higher percentages of activated NK cells, that is, $CD3^- CD56^+$ NK cells, compared to the usual peripheral blood lymphocytes.

Many patients with pancreatic cancer receive treatments with anti-cancer agents, regardless of whether or not they undergo an operation. The survival rate at one year after anti-cancer therapy such as chemotherapy (hereinafter referred to as "one-year survival rate"), when the treatments with anti-cancer agents alone had been administered, was mostly in the range of 15 to 33% (Heinemann, V. et al., BMC Cancer, 2008, 8:82; Tanaka, T. et al., Jpn J Clin Oncol, 2008, 38:755; Okusaka, T. et al., Cancer Chemother Pharmacol, 2008, 61:615; Strumberg, D. et al., 2009 Gastrointestinal Cancers Symposium, Abstract #195; Nakamura, K. et al., Br J Cancer, 2006, 94:1575; Ueno, H. et al., 2007 ASCO, Abstract #4550; Lee, G. et al., 2008 ASCO, Abstract #15577; and Kim, M. Y. et al., Jpn J Clin Oncol, 2009, 39:49). In contrast, Examples comprised of 27 cases in which the immunotherapy of the present invention had been administered showed a one-year survival rate as high as 63%, which was a revolutionary outcome in rapidly advancing pancreatic cancer. In these Examples, the combined use of the immunotherapy of the present invention and anti-cancer agents elicited much better outcomes than the use of the immunotherapy of the present invention alone, in terms of the survival time after starting the immunotherapy of the present invention.

In the immunotherapy of the present invention, the immunotherapeutic agent comprising high percentages of activated NK cells was applied, at predetermined dosages, to particular patients to be treated (the patient with pancreatic cancer who were in a particular immunocompromised state), whereby great improvement in the survival rate was achieved. Levels of the survival rate which were realized were remarkable, which exceeded the range previously expected in the treatment of pancreatic cancer with conventional anti-cancer agents.

However, there are very great variations among individuals in the number of activated lymphocytes obtained by culturing patient's peripheral blood lymphocytes and in the percentage of NK cells contained therein. In addition, there are great differences in the resulting clinical efficacy among individuals, even though administrations are carried out at the same number of activated lymphocytes and at the same percentage of NK Cells. Therefore, it is difficult to show a clear threshold of administration conditions such that effects are definitely achieved in each individual.

The present inventors have found that it is effective to define the conditions of administering the immunotherapeutic agent of the present invention and of patients to whom the immunotherapy of the present invention is done, which provides better outcomes for a group of patients, and not for each individual, with a statistically high probability. The conditions of administration and patients which are characteristic features of the immunotherapy of the present invention have significance as indicators which make it possible to extend, to a great extent, the overall survival time after diagnosis of pancreatic cancer, with a statistically high probability.

In the present invention, the conditions of administration and patients' immune status were determined on the basis of median values in the Examples comprised of 27 patients with pancreatic cancer. The above-described one-year survival rate of 63% was an efficacy which was obtained based on all the Examples. Therefore, if the immunotherapeutic agent of the present invention is administered under conditions of not less than a median value or values in all the Examples, it could be expected that a higher one-year survival rate is statistically achieved. All the Examples included some patients to whom the immunotherapy of the present invention was applied alone, with no anti-cancer agents used in combination therewith. Hence, if an anti-cancer agent is constantly used in combination with the immunotherapeutic agent of the present invention, it would be expected that a higher one-year survival rate can be achieved from the statistical results we have shown. It should be ensured that a one-year survival rate of at least 63% is realized.

In this sense, the concept of "Example" of the present invention as described herein is somewhat different from the general concept of Example. In general, Examples are referred to cases which come under the requirements of the scope of the claims. In the present invention, however, the conditions which, based on a median value in the "Examples," are of not less than the median value have been defined as the requirements of the scope of the claims. As a result, the "Examples" of the present invention include cases which do not always come under the requirements of the scope of the claims (which come under conditions of less than a median value which is obtained in the "Examples"). Those cases may be referred to as reference Examples, but are cases necessary to determine a median value. For this reason, in the specification, all the cases that were carried out to define the requirements of the scope of the claims are designated as "Examples".

It is necessary to make significant immunological impacts on cancerous tissues of rapidly advancing pancreatic cancer and on a body having reduced immune function. The present inventor have found that in the immunotherapy of the present invention, it is effective that the largest possible number of activated lymphocytes is administered at once, the administered activated lymphocytes consisted of at least 30% CD3⁻ CD56⁺ NK cells, and at least four infusions of the activated lymphocytes are administered. The effective number of activated lymphocytes contained in each of the infusions of the immunotherapeutic agent of the present invention is at least $15 \times 10^9$ cells. The cell number is over three times larger than the number of activated lymphocytes administered in conventional immunotherapies in Japan.

It was found that the immune status significantly improved when patients with pancreatic cancer exhibited a decrease in immune status before the initiation of the immunotherapy of the present invention, relative to healthy subjects. The decreased immune status corresponds to at least one of the following conditions:
(a) the number of peripheral blood lymphocytes being less than 1,000 cells/µl;
(b) the number of CD3⁻ CD56⁺ NK cells of the peripheral blood lymphocytes being less than 200 cells/µl;
(c) the cytotoxic activity of CD3⁻ CD56⁺ NK cells in the peripheral blood being less than 30% in a conventional $^{52}Cr$ releasing assay using K562 target cells; and
(d) the number of NKG2D⁺ lymphocytes in the peripheral blood being less than 400 cells/µl.

By examining peripheral blood lymphocytes from a patient to determine these immunological conditions, one can decide the time of starting the administration of the immunotherapeutic agent of the present invention to patients with pancreatic cancer.

In particular, it is most preferable that the immunotherapy is started at the time when the immune status of the patients has decreased down to the threshold value of the range of any of (a) to (d) described above. In the case where the immune status of the patients is maintained at a level similar to that of healthy subjects, immunological impacts resulting from administering the immunological agent of the present invention may be trivial (however, if the immune status of the patients is well maintained before the immunotherapy, their survival time may consequently extend). On the other hand, in the case where the immune status of patients has greatly decreased below a threshold value or values with their worsening general conditions, the immunotherapy of the present invention may be too late to treat pancreatic cancer in many cases.

In addition, the CD4/CD8 ratios of more than 3 in the peripheral blood lymphocytes are an indicator for judging an immunocompromised state.

Further, the administered lymphocytes contain not only CD3⁻ CD56⁺ NK cells (all NK cells have NKG2D) but also either or both of CD4⁺ T cells and CD8⁺ T cells. Because a significant proportion of the CD8⁺ lymphocytes contains NKG2D⁺ cells having cytotoxic activity as well as NK cells, synergistic cytotoxic effects of NK cells and CD8⁺ T cells will be obtained.

DETAILED DESCRIPTION OF THE INVENTION

The immunotherapy of the present invention employs an immunotherapeutic agent comprising, as the main constituent, activated lymphocytes which are obtained by culturing and propagating peripheral blood lymphocytes derived from patients with pancreatic cancer. The immunotherapy is performed by employing the immunotherapeutic agent. The activated lymphocytes contain activated NK cells. These activated NK cells are distinguished by the surface markers, CD3⁻ and CD56⁺, from T cells which are positive for CD3. A high percentage of CD3 CD56⁺ NK cells can be obtained by applying the methods to stimulate and propagate NK cells in peripheral blood lymphocytes, described in Japanese Unexamined Patent Publication No. 2006-340698.

Figure 1:
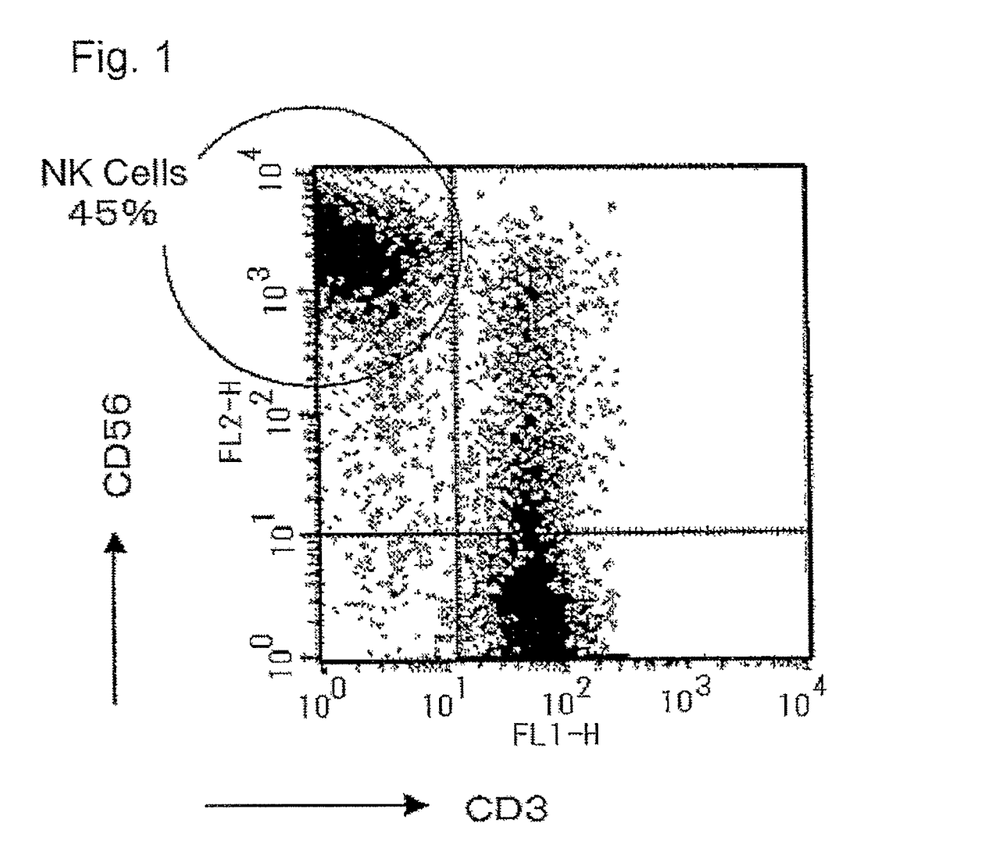
FIG. 1 shows flow cytometric analysis of the activated lymphocytes which were employed in the immunotherapy of the present invention.

FIG. 1 shows flow cytometry of the immunotherapeutic agent of the present invention employed in one Example. In FIG. 1, the abscissa FL1-H represents the fluorescence intensity of the surface marker CD3 and the ordinate FL2-H represents the fluorescence intensity of the surface marker CD56. The circled area indicates CD3³¹ CD56⁺ NK cells. The result demonstrates that the proportion of CD3⁻ CD56⁺ NK cells is about 45% in the activated lymphocytes. There are great variations among individuals in the percentages of CD3⁻ CD56⁺ NK cells contained in the activated lymphocytes after culturing peripheral blood lymphocytes. In the Examples described below, the percentages of CD3⁻ CD56⁺ NK cells widely rangedfrom 10 to 70%. In each of the patients, the percentage of the CD3⁻ CD56⁺ NK cells after culture became higher than that before culture.

Another group of events which were located in the lower middle area in the flow cytometry plot shown in FIG. 1 represents activated T cells. These activated T cells consist predominantly of CD4⁺ T cells and CD8⁺ T cells.

The immunotherapeutic agent of the present invention can be applied to treat patients with pancreatic cancer without an anti-cancer agent or agents. However, in the use of this immunotherapy, more significant efficacy is obtained by a combination of the immunotherapy of the present invention and an anti-cancer agent or agents.

It is preferable that the number of activated lymphocytes contained in each of the infusions is at least $15 \times 10^9$ cells. The cell number is over three times larger than the number of activated lymphocytes administered in conventional immunotherapies in Japan. The highest number of the activated lymphocytes administered in the Examples described below was around $18\times10^9$ cells. It is preferable that the administered lymphocytes contain at least 30% CD3$^-$ CD56$^+$ NK cells. At least four administrations(infusions) of the lymphocytes are required for effective treatment of pancreatic cancer to extend survival time.

Further, it is preferable that the immunotherapy of the present invention is applied to patients with pancreatic cancer who fulfill at least one of the following immunocompromised states:
(a) the number of peripheral blood lymphocytes being less than 1,000 cells/μl;
(b) the number of CD3$^-$ CD56$^+$ NK cells of the peripheral blood lymphocytes being less than 200 cells/μl;
(c) the cytotoxic activity of CD3$^-$ CD56$^+$ NK cells in the peripheral blood being less than 30%; and
(d) the number of NKG2D$^+$ lymphocytes in the peripheral blood being less than 400 cells/μl.

In the Examples described below, it was ascertained that in the four states of (a) to (d) described above, the immune function of the patients with pancreatic cancer was lower than that of healthy subjects with statistically significant differences. In addition, administration of a large number of CD3$^-$ CD56$^+$ NK cells at once to the patients showed a definite increase in their immune state.

The one-year survival rate was 63% in the Examples comprised of 27 cases described below. This survival rate was a much better outcome than that obtained in conventional treatments of pancreatic cancer with anti-cancer agents. In the immunotherapy of the present invention, the number of activated lymphocytes and the percentage of CD3$^-$ CD56$^+$ NK cells contained in each of the infusions were defined on the basis of the respective median values in all the Examples. That is, for the number of activated lymphocytes and the percentage of CD3$^-$ CD56$^+$ NK cells to be administered, the ranges of not less than the respective median values were defined. Therefore, if these median values are used as the lowest values to apply the immunotherapy of the present invention to patients, it would be expected that a one-year survival rate that is still higher than 63%, which was obtained in all the Examples, can be achieved. Incidentally, a median value is essentially a measurement, and thus, in a strict sense, its significant figures should be taken into consideration. In the present invention, however, a median value is accepted as an "indicator" for achieving a higher survival rate, and consequently, an approximate numerical value of 63% is used regardless of the significant figures of a median value.

Further, it is preferable that the immunotherapy of the present invention is administered to patients with pancreatic cancer having the CD4/CD8 ratios of more than 3 in the peripheral blood lymphocytes. The decrease in CD8$^+$ T cells also represents an indicator of an immunocompromised state. Therefore, the CD4/CD8 ratio in patients with pancreatic cancer is often higher than that in healthy subjects.

In long-term survivors (who survived for a period of 10 months or more after starting the immunotherapy of the present invention), a remarkable increase in the number of NKG2D$^+$ lymphocytes in the peripheral blood was observed after the immunotherapy. We further found substantial increases in the number of peripheral blood lymphocytes, the number of NK cells, and the NK activity, and decreases in the CD4/CD8 ratio. In short-term survivors (who died within 5 months after the immunotherapy of the present invention), there were no significant differences in these parameters between before and after the immunotherapy. From these facts, it was suggested that the immunotherapy of the present invention would rapidly improve and enhance immune function which was deteriorated in the presence of pancreatic cancer, thereby leading to the extension of survival time.

With the exception of end-stage patients, the degree of rapid enhancement of immune function by the immunotherapy of the present invention was found to be greatly varied in individuals. Therefore, to get clinical effects in each individual, it is difficult to precisely show the number of times of administration, the number of cultured lymphocytes containing activated NK cells to be administered, or the value of patients' immune status described above. However, if the immunotherapeutic agent of the present invention is administered according to the above-described conditions of administration and patients' immune status, it could be expected that a one-year survival rate will be statistically and stochastically higher than 63%. This is due to the fact that the above-described conditions of administration and patients' immune status are defined using, as the lowest values, the respective median values of the number of administrations and immunological conditions in the group of Examples showing a one-year survival rate of 63%.

EXAMPLES (1) Procedures of culturing and propagating lymphocytes
Culturing and propagating of peripheral blood lymphocytes of patients with pancreatic cancer were carried out by the following steps.
Step 1: In 20 ml of phosphate buffered saline (PBS) were dissolved an anti-CD3 antibody (0.1 μl/ml, Orthoclone OKT3, available from JANSSEN PHARMACEUTICAL K.K.) and an anti-CD52antibody (20 to 40 μl/ml, MAB-CAMPATH, available from Bayer).
Step 2: The solution of step 1 was placed in a 225-cm$^2$ flask overnight at 4° C.
Step 3: The antibody-coated flask was washed twice with PBS.
Step 4: Thirty ml of heparinized peripheral blood was taken from a patient with pancreatic cancer and peripheral blood mononuclear cells (PBMCs) were separated by density-gradient centrifugation using Ficoll-Paque Plus (available from Amersham Pharmacia Biotech).
Step 5: The PBMCs separated in step 4 were suspended at a concentration of 0.5 to $1\times10^6$ cells/ml in cell culture medium KBM-NKCGM-1 (available from KOHJIN BIO, Co. Ltd.) supplemented with IL-2 (500 units/ml, available from Chiron), to which 2 to 10% of the patient's plasma was further added. At this step, the volume of culture medium is 60 to 120 ml. PBMCs suspended in the culture medium were added to the antibody-coated flask prepared in step 3, and then cultured at 37° C. in a 5% CO$_2$ incubator. The patient plasma may be replaced with serum obtained from a healthy subject.
Step 6: When many colonies and blast formation were observed at three to five days after the initiation of culture, culture was fed with fresh medium (20-100% of the initial volume) containing IL-2 (500 units/ml). This stage was usually at three days after the culturing was begun.
Step 7: At one to three days (in many cases, one day) after adding fresh medium in step 6 and entering the exponential growth phase, the cultured medium containing activated lymphocytes was transferred into a KBM-NKCGM-1B (a bag containing one liter of KBM-NKCGM-1 medium). The cultured medium was usually dispensed into two to three bags. At intervals of three to four days after dispensing, 100 to 300 ml of KBM-NKCGM-1 and 10,000 to 20,000 units of IL-2 were added per bag.

Step 8: At 14 to 21 days in culture (22-day or longer culture often resulted in reduced activity), the medium was transferred into centrifugation tubes, which were subjected to centrifugation at 600 G for 10 minutes. The supernatants were aspirated from the tubes, leaving the pellets. Then, PBS was added to the pellets for washing, and centrifugation was performed again. These procedures were repeated two to three times so as to sufficiently wash the cultured lymphocytes. Finally, the pellets were collected and suspended in 100 ml of physiological saline solution, to which 2 to 4% of human serum albumin was added. It was ascertained that sterility and endotoxin tests gave negative results.

(The lymphocytes-suspending solution thus obtained was administered to a patient from whom the original lymphocytes were derived via a peripheral vein for 30 to 60 minutes, within four hours after preparation.)

Step 9 (analysis of constituents): For the lymphocytes suspended in physiological saline solution, given numbers of cells were taken into Eppendorf tubes, to which fluorescein-labeled antibodies were added, followed by staining the cells in routine procedures. The stained cells were immediately analyzed by flow cytometry to determine the percentages of CD3− CD56+ NK cells, CD4− T cells, and CD8+ T cells (see FIG. 1).

(2) Characteristics of Activated Lymphocytes After Culture and Propagation

Flow cytometry of the activated lymphocytes after culture and propagation provided the following results.

High levels of expression of CXCR3 chemokine receptors, NKG2D, and TRAIL were found on the cell surface of NK and T cells contained in the activated lymphocytes. NKp30, NKp44, and NKp46, activating receptors selectively expressed by human NK cells, were also found on NK cells in the activated lymphocytes. Although it is known that expression of signal transduction molecules on NK cells, CD3ζ chain, DAP12, FcεR1 was low or negative in patients with cancer, the expression was restored in the propagated NK cells. In addition, the NK cells exhibited continuous production of IFN-γ and high levels of cytotoxicity (with a routine method targeted to K562) were maintained for a period of up to at least three weeks in culture. Specifically, when NK cells were purified from 21-day cultured lymphocytes and the cytotoxic activity of the purified cells was measured, the purified NK cells exhibited high cytotoxic activity, with an E/T ratio at 50% lysis being 1.07 (the lower its value, the higher activity it indicates). For comparison, activated lymphocytes which were stimulated and cultured with a CD3 antibody showed an E/T ratio of 71.45.

(3) Procedures of Administration to Patients with Pancreatic Cancer

The lymphocytes suspended in physiological saline solution were administered to a patient with pancreatic cancer via a peripheral vein for 30 to 60 minutes, within four hours after step 8 in the above-described procedures of culturing and propagating lymphocytes.

(4) Results of Patients with Pancreatic Cancer Treated with the Immunotherapeutic Agent of the Present Invention (4-1) Results of the Overall and Post-Treatment Survival Times The upper rows in Table 1 indicate the results of the overall time and one-year survival rate of patients with pancreatic cancer to whom the immunotherapy of the present invention was applied (Examples). These results were based on the medical records of all the cases from the first diagnosis of pancreatic cancer to the time of April, 2009. Every case received four or more administrations of the immunotherapeutic agent of the present invention. Other cases which received less than four administrations were not included in the Examples, because the patients of these cases died within two months from the initiation of the immunotherapy, due to the fact that they showed ECOG PS (Eastern Cooperative Oncology Group performance statuses, abbreviated hereinafter as "PS") of 3 to 4, had poor general conditions, and were at a terminal stage. Of 27 cases which were the Examples of the present invention, 21 cases received the combined use of the immunotherapy of the present invention and anti-cancer agents. Six cases were treated only with the immunotherapy of the present invention without the use of anti-cancer agents.

The eight studies in the lower rows in Table 1, which represent Comparative Examples, show the results of the overall time and one-year survival rate of patients with pancreatic cancer who were treated with ant-cancer agents alone (which are described in the references: Heinemann, V. et al., BMC Cancer, 2008, 8:82; Tanaka, T. et al., Jpn J Clin Oncol, 2008, 38:755; Okusaka, T. et al., Cancer Chemother Pharmacol, 2008, 61:615; Strumberg, D. et al., 2009 Gastrointestinal Cancers Symposium, Abstract #195; Nakamura, K. et al., Br J Cancer, 2006, 94:1575; Ueno, H. et al., 2007 ASCO, Abstract #4550; Lee, G. et al., 2008 ASCO, Abstract #15577; and Kim, M. Y. et al., Jpn J Clin Oncol, 2009, 39:49). The anti-cancer agents used in these Comparative Examples were gemcitabine hydrochloride (GEM) or S-1, or combinations thereof.

As shown in Table 1, the Examples (27 cases) exhibited a median overall survival time of 14.0 months and a one-year survival rate of 63%, while in the Comparative Examples, many studies showed one-year survival rates in the range of 15 to 33%, with one study showing the highest one-year survival rate, 54%. Of 27 cases which were the Examples of the present invention, for sub-groups of "in combination with an anti-cancer agent," "no pancreas resection," "no pancreas resection and PS: 0-1," "PS: 2-3," and "metastasis (stage IVb)," calculations of the respective overall survival times and one-year survival rates gave better results in any of these sub-groups than those in the Comparative Examples. These results demonstrated that the immunotherapy of the present invention, and more preferably the combined use of the immunotherapy of the present invention and anti-cancer agents extended the overall survival time and increased the one-year survival rate to a greater extent than the administration of anti-cancer agents alone.

TABLE 1

Survival Times After Diagnosis Of Pancreatic Cancer

| | | Number of Cases | Overall Survival Time (median, months) | One-Year Survival Rate (%) | Non-Patent Document No. |
|---|---|---|---|---|---|
| Examples: Immunotherapeutic + anti-cancer agents (21 cases) | Overall cases | 27 | 14.0 | 63 | |
| | With, anti-cancer agents | 21 | 14.0 | 62 | |
| | No resection | 19 | 12.0 | 58 | |

TABLE 1-continued

Survival Times After Diagnosis Of Pancreatic Cancer

|  |  |  | Number of Cases | Overall Survival Time (median, months) | One-Year Survival Rate (%) | Non-Patent Document No. |
|---|---|---|---|---|---|---|
| Immunotherapeutic agent alone (6 cases) |  | No resection (PS: 0-1) | 11 | 15.0 | 64 |  |
|  |  | PS 2-3 | 12 | 11.5 | 58 |  |
|  |  | Metastasis (IVb) | 14 | 14.5 | 64 |  |
| Comparative Examples: Anti-cancer agents alone | GEM | Mainly, PS: 0-1, IVb | Meta-analysis | 5-8 | 15-25 | 1 |
|  | GEM | Mainly, PS: 0-1, IVb | 264 | 6.8 | 21.6 | 2 |
|  | S-1 | Mainly, PS: 0-1, IVb | 40 (multi-center) | 9.2 | 32.5 | 3 |
|  | S-1 | Mainly, PS: 0-1, IVb | 27 | 9.1 | — | 4 |
|  | GEM + S-1 | Mainly, PS: 0-1, IVb | 33 | 12.5 | 54 | 5 |
|  | GEM + S-1 | Mainly, PS: 0-1, IVb | 54 (multi-center) | 10.1 | 33 | 6 |
|  | GEM + S-1 | Mainly, PS: 0-1, IVb | 32 | 8.4 | — | 7 |
|  | GEM + S-1 | Mainly, PS: 0-1, IVb | 22 | 8.5 | 27.3 | 8 |

The upper panel (a) of Table 2 indicates detailed data of the Examples (27 cases) shown in Table 1 and of Comparative Examples (9 cases) receiving less than four administrations. Eight cases of the Comparative Examples in Table 2 already were at an end stage with PS 3-4 when the immunotherapy of the present invention was begun. Therefore, they were thought to die within a short period since the number of administrations was not enough for effective treatment of pancreatic cancer. In the Examples, the overall survival time was 14.0 months and the survival time after the immunotherapy of the present invention was 9.0 months. The post-immunotherapy survival time in the Examples was clearly longer than that in the Comparative Examples (significant difference, p=0.00001, by the Mann-Whitney test).

The lower panel (b) of Table 2 indicates detailed data of 12 survivors shown in the Examples in panel (a), at the time of April, 2009. Although metastasis was found in 10 of the 12 cases, the median overall survival time was 18.0 months and the post-immunotherapy median survival time was 13.5 months. These cases included patients who exhibited post-immunotherapy survival times of 10.0 months or more (long-term survivors), as described below. These long-term survivors were found to make a rapid and remarkable recovery of immune function (as described below).

TABLE 2

(a) Examples And Comparative Examples (Less Than Four Administrations) Using The Immunotherapeutic Agent

|  | Examples | Comparative Examples |
|---|---|---|
| Overall cases | 27 | 9 |
| Total number of administrations | 4- | 1-3 |
| Median number of administrations | 13 | 2 |
| Overall survival time (median, months) | 14.0 (95% CI: 11.4-19.9) | 6.5 (95% CI: 1.7-20.8) |
| Post-immunotherapy survival time (median, months) | 9.0 (95% CI: 7.6-12.4) | 1.0 (95% CI: 0.7-1.7) |
| One-year survival time | 63.0% | 33.3% |
| Survivors (in April, 2009) | 12/27 (40.7%) | 1/9 (11.1%)* |

(b) Details On Survivors in The Examples (April, 2009)

| Total Survivors | Metastasis | Overall Survival Time (median) | Post-immunotherapy Survival Time (median) |
|---|---|---|---|
| 12 | 10 | 18.0 (95% CI: 12.7-28.6) | 13.5 (95% CI: 9.4-17.7) |

*At the time of investigation, the survivor was at 2 months after the treatment was begun.

Table 3 summarizes PS at the time of starting the immunotherapy and post-immunotherapy survival times for the Examples (27 cases). They were divided into two groups, group 1 showing PS0~1 and group 2 showing PS 2~3, and then compared. "CI" denotes a confidence interval. Although groups 1 and 2 had different median values in the overall survival time, there was no significant difference (the Mann-Whitney test) between the 2 groups in the overall survival time, and in the post-immunotherapy survival time. PS 2~3 indicates poor general conditions, compared to PS0~1. However, group 2 would attain survival time similar to that in group 1, if the combined use of the immunotherapy of the present invention and anti-cancer agents is possible, as described below.

TABLE 3

The Number Of Cases Having The Respective PS At The Time Of Starting The Immunotherapy And Their Survival Times

| ECOG PS |  | Number of Cases | Overall Survival Time | Post-immunotherapy Survival Time |
|---|---|---|---|---|
| Group 1 | 0 | 1 (1) | 17.0 | 10.0 |
|  | 1 | 14 (12) | (95% CI: 10.9-23.6) | (95% CI: 7.2-14.3) |
| Group 2 | 2 | 9 (6) | 11.5 | 9.0 |
|  | 3 | 3 (2) | (95% CI: 7.5-20.0) | (95% CI: 5.3-13.2) |

( ): cases in which the an anti-cancer agent(s) was used in combination with the immunotherapy of the present invention Table 4 shows the survival times corresponding to the use of anti-cancer agents at the time of starting the immunotherapy of the present invention for the Examples (27 cases).

Group 1 represents "no anti-cancer agents" or "after anti-cancer agents became ineffective." Group 2 represents "combined use of anti-cancer and immunotherapeutic agents." Between groups 1 and 2, no difference was found in the overall survival time, but there was a significant difference in the post-immunotherapy survival time that is survival time after the initiation of the immunotherapy, (p<0.05, t-test by the Welch method). This indicates that the combined use of the immunotherapy of the present invention and anti-cancer agents produced synergistic effects, contributing to the extension of survival time. When compared to the Comparative Examples in Table 1, in which the anti-cancer agents were used alone, group 1 also showed much better results, and provided sufficient effects, even though the immunotherapy of the present invention was administered alone.

For group 2 in Table 4, the survival time for each of anti-cancer agents used was further examined. Although it was impossible, due to a small number of cases, to make a statistical analysis of the survival times, S-1alone gave a longer median overall survival time than GEM (gemcitabine) alone.

Furthermore, the combined use of GEM and S-1 gave a longer median overall survival time than S-1 alone.

TABLE 4

Use Of Anti-Cancer Agents At The Time Of Starting The Immunotherapy And Survival Times

| | Use patterns of anti-cancer agents at the time of starting the immunotherapy | Number of Cases | Overall Survival Time | Post-immunotherapy Survival Time |
|---|---|---|---|---|
| Group 1 | No anti-cancer agents/After anti-cancer agents became ineffective | 6 | 15.5 (95% CI: 8.5-24.8) | 5.5** (95% CI: 3.3-8.7) |
| | *Concurrent use in combination with anti-cancer agent | 21 | 14.0 (95% CI: 10.9-21.1) | 10.0** (95% CI: 8.2-14.1) |
| | ***GEM alone | (12) | 10.5 (95% CI: 7.9-14.1) | 8.5 (95% CI: 5.9-10.6) |
| Group 2 | S-1 alone (3 cases after GEM was ineffective) | (4) | 21.0 (95% CI: 4.4-38.6) | 17.0 (95% CI: 0.0-26.1) |
| | GEM + S-1 (2 cases after GEM was ineffective) | (4) | 17.5 (95% CI: 3.2-26.3) | 13.5 (95% CI: 1.2-21.5) |
| | GEM + oxaliplatin | (1) | 37.0 | 26.0 |

*The immunotherapy of the present invention was co-administered within 2 months before and after the use of anti-cancer agents.
**P < 0.05, t-test by the Welch method
***GEM: gemcitabine Table 5 summarizes detailed data of the Examples (27 cases) and long-term survivors. Eleven cases in the Examples are the long-term survivors (LST: Long Survival Time) who survived for a period of 10.0 months or more after starting the immunotherapy of the present invention. The long-term survivors will be designated as "preferable Examples" in a sense that particularly good results were achieved in the Examples. (The meaning of "preferable Examples" in this specification is based only on results, and those practicing conditions are the same as those of the other Examples. Therefore, its meaning is somewhat different from the general meaning of preferable Example. To put it another way, it represents a "preferable Examples for reference.")

As shown in Table 5, there were found no remarkable differences in clinical backgrounds (stage, PS, with or without resection, combined use of immunotherapeutic and anti-cancer agents) between the working and preferable Examples. This means that the patients in the preferable Examples were clinically not in a particularly good state, compared to those in the other Examples. Thus, this supports the fact that significant improvements in the overall survival time and one-year survival rate in the Examples of the present invention in Table 1 do not result from patients having good clinical conditions. Better outcomes in the Examples of the present invention in Table 1 result from the constitution of the present invention administrating the immunotherapeutic agent according to the predetermined conditions for administration and patient's immune status.

TABLE 5

Comparison Of Examples And Long-Term Survivors (Preferable Examples)

| | Examples | Long-term survivors |
|---|---|---|
| Number of Cases | 27 | 11 (Survivors 8) |
| Post-immunotherapy Survival Time (median, months) | 9.0 (95% CI: 7.6-12.4) | 15.0 (95% CI: 12.3-19.3) |

TABLE 5-continued

Comparison Of Examples And Long-Term Survivors (Preferable Examples)

| | Examples | Long-term survivors |
|---|---|---|
| Stage IVb (%) | 51.8 | 45.5 |
| PS0-1 (%) | 55.6 | 72.7 |
| Pancreas Resection (%) | 29.6 | 26.7 |
| Irradiation (%) | 18.5 | 18.2 |
| In combination with anti-cancer agent (%) | 77.8 | 100 |

(4-2) Determination of Immunological Changes in the Examples
<Measuring Procedures>

Immunological changes could be determined between before and after the immunotherapy of the present invention in 24 of 27 patients with pancreatic cancer except for some parameters.

Peripheral blood was taken just before the initiation of the immunotherapy. Treatments were performed by administrating four or more infusions of the immunotherapeutic agent of the present invention, and peripheral blood was taken at intervals of 1 to 2 months within 6 months after the immunotherapy.

Measurements were the following.
1. The number of lymphocytes administered at each of the infusions.
2. The percentage of $CD3^- CD56^+$ NK cells contained in the lymphocytes administered at each of the infusions.
3. The number of peripheral blood lymphocytes.
4. The number of $CD3^- CD56^+$ NK cells in the peripheral blood lymphocytes.
5. The cytotoxic activity of NK cells in the peripheral blood lymphocytes.
6. The number of $NKG2D^+$ lymphocytes in the peripheral blood.
7. The CD4/CD8 ratio in the peripheral blood lymphocytes.

The number of lymphocytes administered and the percentage of NK cells therein, as well as the numbers of lymphocytes and NKG2D+ lymphocytes in peripheral blood, and the CD4/CD8 ratios before and after the treatment were examined by flow cytometry using whole blood or cultured lymphocytes stained with fluorescence-labeled antibodies.

For the NK activity, a method was employed in which the cytotoxic activity against tumor cell K562 labeled with $^{51}Cr$ was determined (which was contracted out to SRL. Inc.).

The numbers of lymphocytes administered and the percentages of NK cells therein at respective infusions were averaged, respectively, to calculate the respective numerical values per infusion.

When peripheral blood was analyzed several times after the immunotherapy, the most different measurement value, relative to the measurement value just before the initiation of the immunotherapy, was used as a value for comparison.

As normal controls, for 24 age-matched healthy subjects (a median age of 61, in the range of 53 to 72 years old) were also examined. Their peripheral bloods were taken and the same parameters as in the Examples were measured. These results are shown as Comparative Examples 1 to 24 in Table 6.

Measurement Results of the Comparative Examples (Healthy Subjects)

Measurement Results of the Comparative Examples (Healthy Subjects)

Table 6 summarizes measurement results of peripheral blood lymphocytes of Comparative Examples (healthy subjects) 1 to 24. Graphs plotting the measurement values of the respective parameters in Table 6 are shown in FIG. 4 to FIG. 8, as described below.

TABLE 6

Numbers Of Peripheral Blood Lymphocytes And Others Of Healthy Subjects

| Comparative Examples | Lymphocytes ($\times 10^2/\mu l$) | NK Cells (/$\mu l$) | NK Activity (%) | NKG2D+ Cells (/$\mu l$) | CD4/CD8 |
|---|---|---|---|---|---|
| 1 | 17 | 311 | 56 | 570 | 3.3 |
| 2 | 14 | 248 | 63 | 389 | 5.6 |
| 3 | 14 | 253 | 51 | 945 | 0.6 |
| 4 | 23 | 262 | 22 | 842 | 2.1 |
| 5 | 11 | 215 | 56 | 518 | 1.6 |
| 6 | 31 | 294 | 23 | 564 | 5.3 |
| 7 | 28 | 398 | 48 | 1240 | 2.2 |
| 8 | 18 | 335 | 27 | 597 | 6.3 |
| 9 | 14 | 179 | 60 | 734 | 1.8 |
| 10 | 23 | 175 | 60 | 711 | 2.5 |
| 11 | 8 | 321 | 19 | 320 | 3.2 |
| 12 | 12 | 411 | 50 | 572 | 2.2 |
| 13 | 18 | 367 | 53 | 805 | 3.0 |
| 14 | 24 | 214 | 47 | 1154 | 1.9 |
| 15 | 21 | 378 | 38 | 552 | 3.4 |
| 16 | 18 | 186 | 53 | 364 | 2.4 |
| 17 | 16 | 405 | 59 | 713 | 2.9 |
| 18 | 16 | 262 | 30 | 704 | 2.4 |
| 19 | 14 | 370 | 61 | 624 | 2.7 |
| 20 | 16 | 378 | 39 | 745 | 3.0 |
| 21 | 16 | 312 | 53 | 629 | 1.1 |
| 22 | 21 | 260 | 26 | 882 | 0.8 |
| 23 | 15 | 454 | 39 | 811 | 1.9 |
| 24 | 28 | 260 | 36 | 591 | 1.0 |

Measurement Results of the Examples (Patients with Pancreatic Cancer)

Numbers of Lymphocytes Administered and Percentages of NK Cells:

Table 7 summarizes the numbers of lymphocytes administered per infusion, the NK cell percentages, the overall survival times, and the post-immunotherapy survival times in 24 of 27 cases which were the Examples of the present invention (patients with pancreatic cancer). (Immunological measurements could not be gotten from three cases of the Examples.)

In Table 7, eleven cases of the Examples having a number with the thick border represent the preferable Examples of the present invention (long-term survivors). (The same also applies in the subsequent tables).

Figure 2:
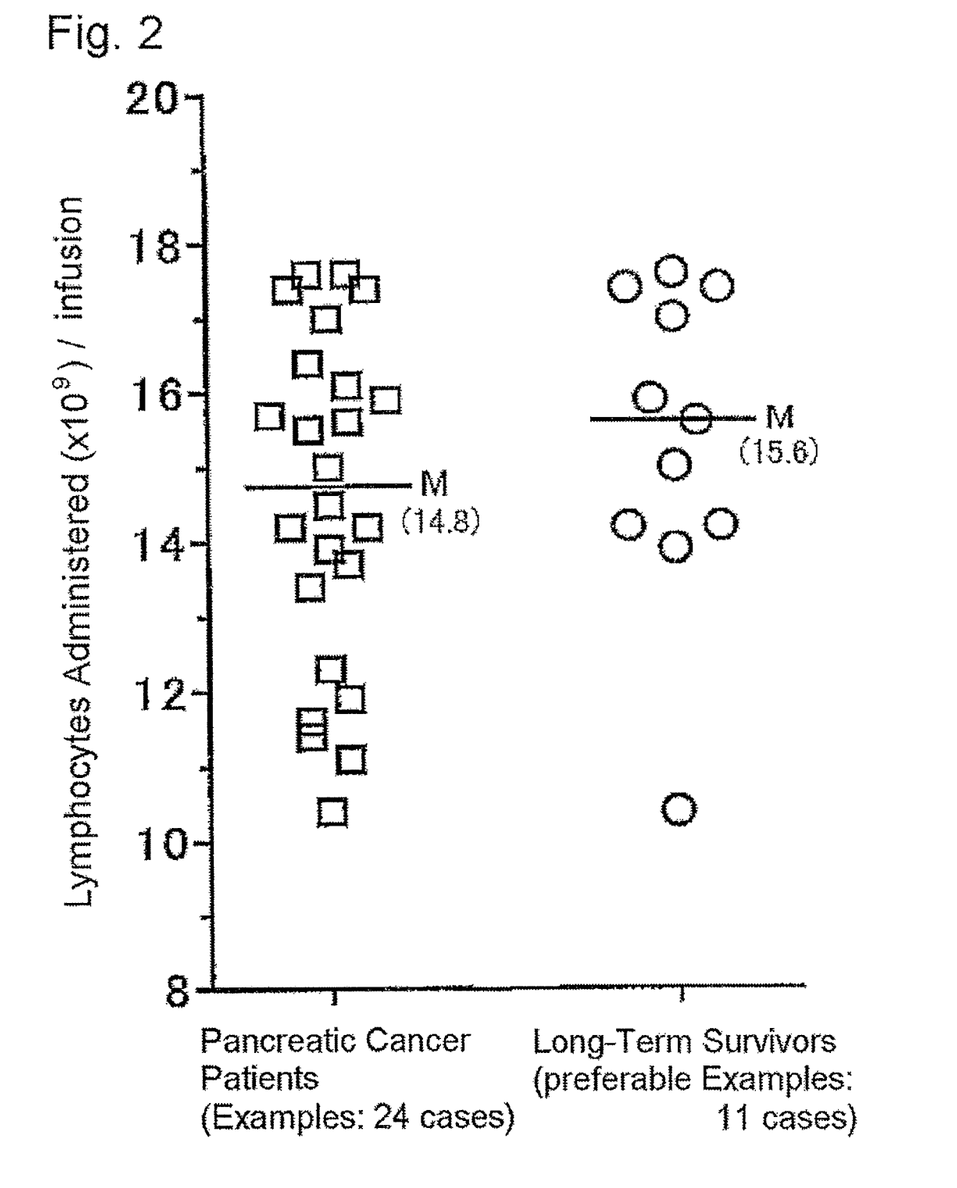
FIG. 2 is a graph plotting the numbers of lymphocytes administered in Table 7 for the Examples and for the preferable Examples in the respective columns.

In FIG. 2, the numbers of lymphocytes administered in Table 7 are plotted for the Examples and for the preferable Examples in the respective columns. "M" denotes a median value. (The same applies in the subsequent figures.)

The numbers of lymphocytes administered in all the Examples were distributed in the range of $10.4 \times 10^9$ to $17.6 \times 10^9$ cells per infusion, with a median value of $14.8 \times 10^9$ cells per infusion. Since the number of lymphocytes which were obtained by culturing and propagating peripheral blood lymphocytes varied in a wide range from individual to individual, it was difficult to clearly define a preferable numerical range of the number of lymphocytes administered. As shown in Tables 1 and 2, however, the one-year survival rate in all the Examples was high with 63%, compared to that obtained by treatments using anti-cancer agents alone. Therefore, it is presumed that >63% one-year survival rate could be statistically achieved by administering lymphocytes of at least a median value, $14.8 \times 10^9$ cells per infusion, or to put it another way, about $15 \times 10^9$ cells per infusion. For this reason, the median value in all the Examples was adopted as the lower limit of the number of lymphocytes administered, in order to ensure effects of the present invention, and thus the number of lymphocytes administered was defined as at least $15 \times 10^9$ cells per infusion.

Figure 3:
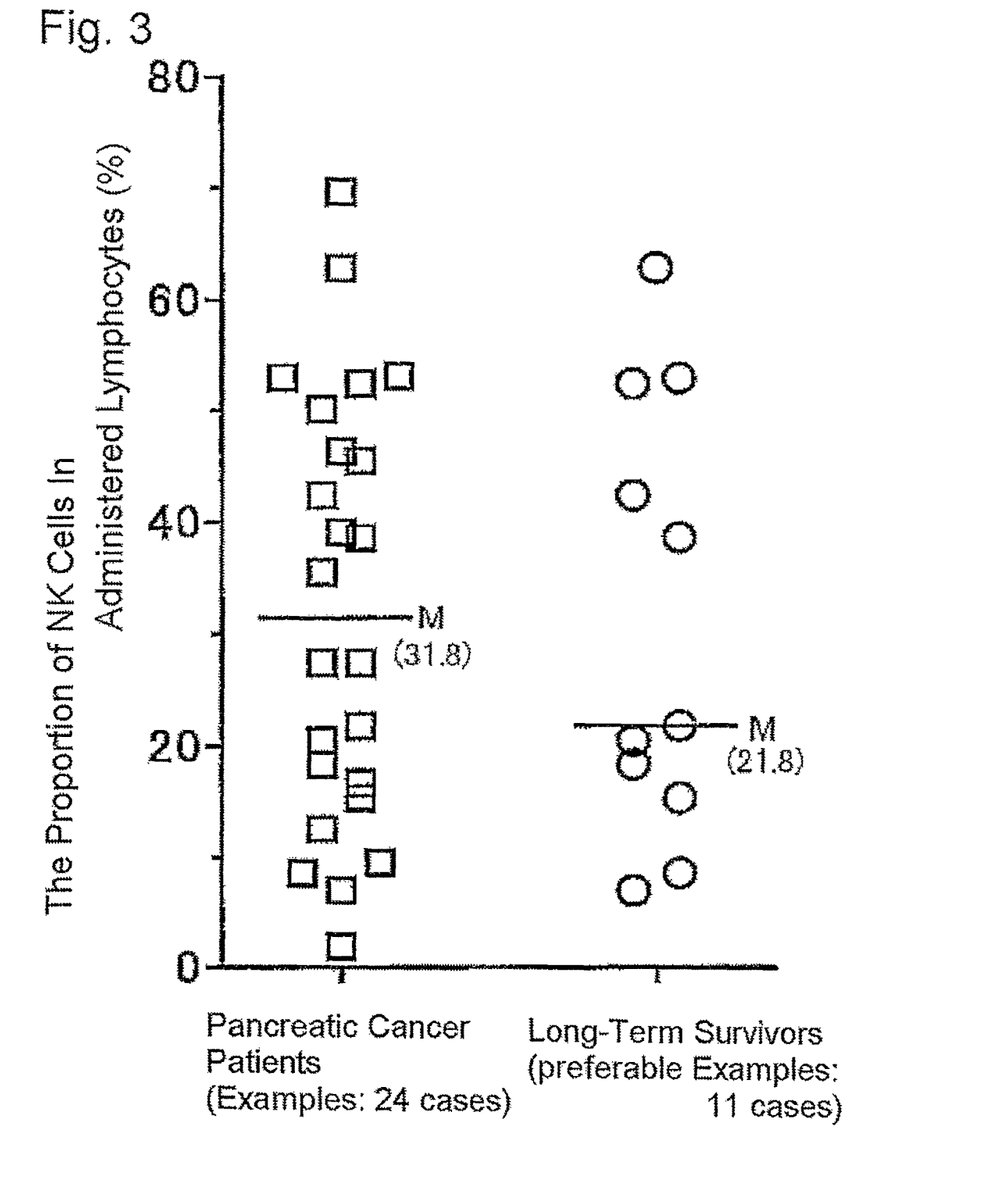
FIG. 3 is a graph plotting the percentages of NK cells in Table 7 for the Examples and for the preferable Examples in the respective columns.

FIG. 3 shows the NK cell percentages in Table 7 for the Examples and for the preferable Examples in the respective columns. The NK cell percentages in all the Examples were distributed in a wide range of 1.9 to 69.9%, with a median value of 31.8%, or to put it another way, about 30%. Similar to the number of lymphocytes administered, the NK cell percentage varied in a very wide range from individual to individual. Therefore, the median value in all the Examples was accepted as the lower limit of the NK cell percentage preferable to almost certainly obtain effects of the present invention, and thus the NK cell percentage was defined as at least 30%.

There were found no significant differences in the number of lymphocytes administered and in the NK cell percentages between all the Examples and a subgroup thereof, long-term survivors (by the Kruskal-Wallis test). This indicates the validity of employing the measurements of all the Examples in defining the number of lymphocytes administered and the NK cell percentages.

TABLE 7

Number Of Lymphocytes Administered To Patients with Pancreatic Cancer, NK Cell Percentages, And Survival Times

| Examples | Lymphocytes Administered ($\times 10^9$ cells/infusion) | NK Cell Percentage (%) | Overall Survival Time (Month) | Post-immunotherapy Survival Time (Month) |
|---|---|---|---|---|
| 1* | 15.6 | 62.9 | 17 | 11 |
| 2 | 14.5 | 46.3 | 24 | 3 |
| 3* | 15.9 | 42.4 | 37 | 26 |
| 4* | 14.2 | 52.9 | 24 | 22 |
| 5* | 14.2 | 21.8 | 18 | 16 |
| 6* | 17.4 | 15.4 | 52 | 19 |
| 7 | 15.5 | 69.6 | 5 | 3 |
| 8 | 17.6 | 50.1 | 4 | 2.5 |

TABLE 7-continued

Number Of Lymphocytes Administered To Patients with Pancreatic Cancer, NK Cell Percentages, And Survival Times

| Examples | Lymphocytes Administered (×10⁹ cells/ infusion) | NK Cell Percentage (%) | Overall Survival Time (Month) | Post-immunotherapy Survival Time (Month) |
|---|---|---|---|---|
| 9* | 13.9 | 8.6 | 18 | 15 |
| 10* | 17.0 | 7.0 | 18 | 15 |
| 11* | 17.6 | 52.4 | 20 | 16 |
| 12* | 15.0 | 18.4 | 12 | 11 |
| 13 | 11.1 | 27.4 | 27 | 9 |
| 14 | 13.7 | 35.5 | 6 | 5 |
| 15* | 17.4 | 38.6 | 21 | 12 |
| 16* | 10.4 | 20.5 | 14 | 10 |
| 17 | 13.4 | 53.1 | 11 | 8 |
| 18 | 15.7 | 1.9 | 9 | 9 |
| 19 | 11.4 | 27.4 | 10 | 8 |
| 20 | 11.6 | 16.7 | 12 | 9 |
| 21 | 12.3 | 39.1 | 16 | 4 |
| 22 | 16.1 | 12.6 | 14 | 7 |
| 23 | 11.9 | 9.5 | 8 | 4 |
| 24 | 16.4 | 45.5 | 6 | 4 |

*preferable Examples

Numbers of Peripheral Blood Lymphocytes:

The left column of Table 8 represents measurement values of the number of peripheral blood lymphocytes before and after the treatments of 24 cases in the Examples of the present invention (patients with pancreatic cancer).

Figure 4:
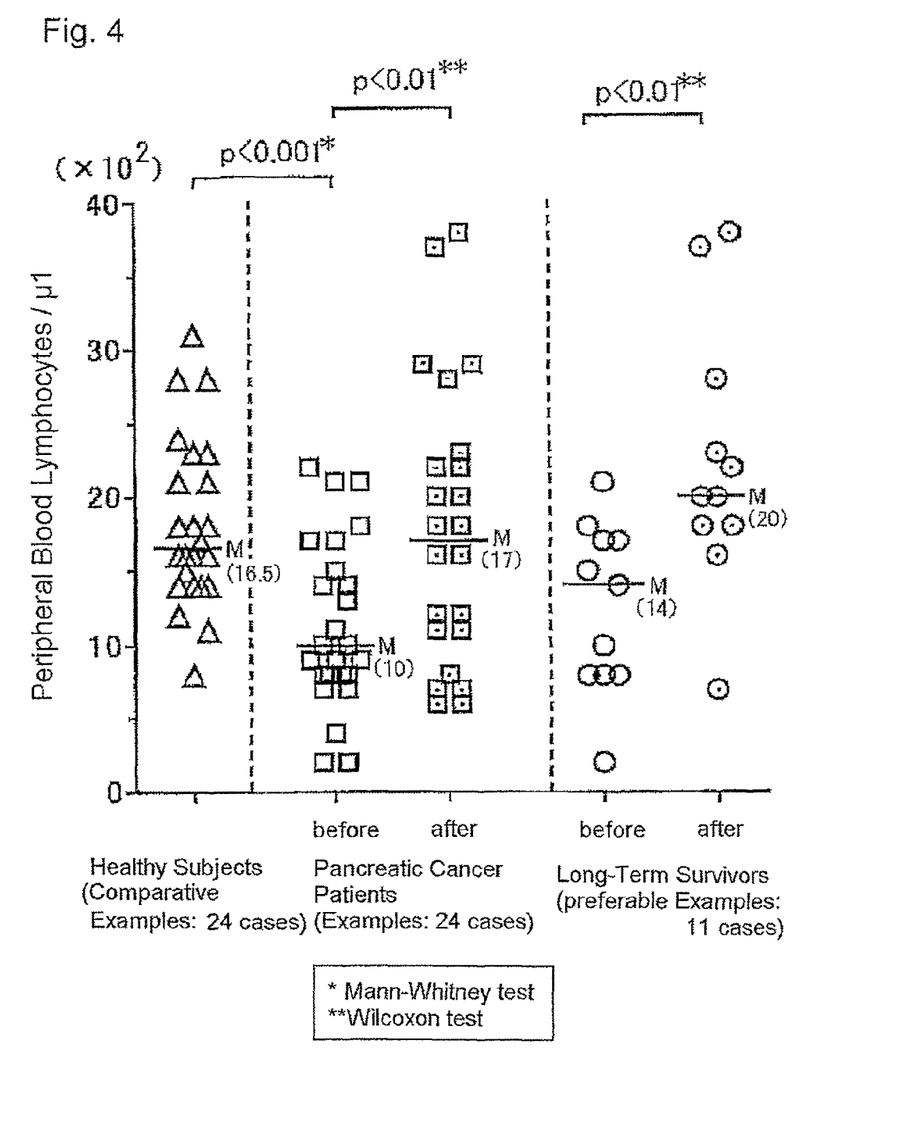
FIG. 4 is a graph plotting the numbers of peripheral blood lymphocytes in the Comparative Examples (healthy subjects) in Table 6 and in the Examples (all the pancreatic cancer patients) and preferable Examples (long-term survivors) in Table 8 in the respective columns.

FIG. 4 is a graph plotting the numbers of peripheral blood lymphocytes in the Comparative Examples (healthy subjects) in Table 6 and in the Examples (all the patients with pancreatic cancer) and preferable Examples (long-term survivors) in Table 8 in the respective columns.

Before the initiation of the immunotherapy of the present invention, the Examples exhibited significantly lower numbers of peripheral blood lymphocytes than the Comparative Examples ($p<0.001$, by the Mann-Whitney test). The median value of the initial numbers of the lymphocytes in the Examples was 1,000 cells/μl. The median value obtained from these clinical data can be employed as an indicator for deciding when the immunotherapy of the present invention should be begun. For example, when the number of peripheral blood lymphocytes of a patient has decreased to below 1,000 cells/μl, the patient will be judged to be in an immunocompromised state, so that the immunotherapy of the present invention will be begun.

The number of lymphocytes in the Examples after the immunotherapy of the present invention increased to significantly higher levels than that before the initiation of the immunotherapy of the present invention ($p<0.01$, by the Wilcoxon test). The number of lymphocytes in the Examples after the immunotherapy reached similar levels to that in the Comparative Examples.

In 6 cases of the preferable Examples (11 cases), the numbers of peripheral blood lymphocytes were more than 1,000 cells/μl before the initiation of the immunotherapy, and further increased after the immunotherapy ($p<0.01$, by the Wilcoxon test). Ten cases of the preferable Examples (91%) exhibited lymphocytes of 1,800 cells/μl or more, but no significant difference was found between the preferable and Comparative Examples.

Numbers of CD3⁻ CD56⁺ NK cells in peripheral blood:
The middle column of Table 8 represents the number of NK cells before and after the treatments of 24 cases in the Examples of the present invention (patients with pancreatic cancer).

Figure 5:
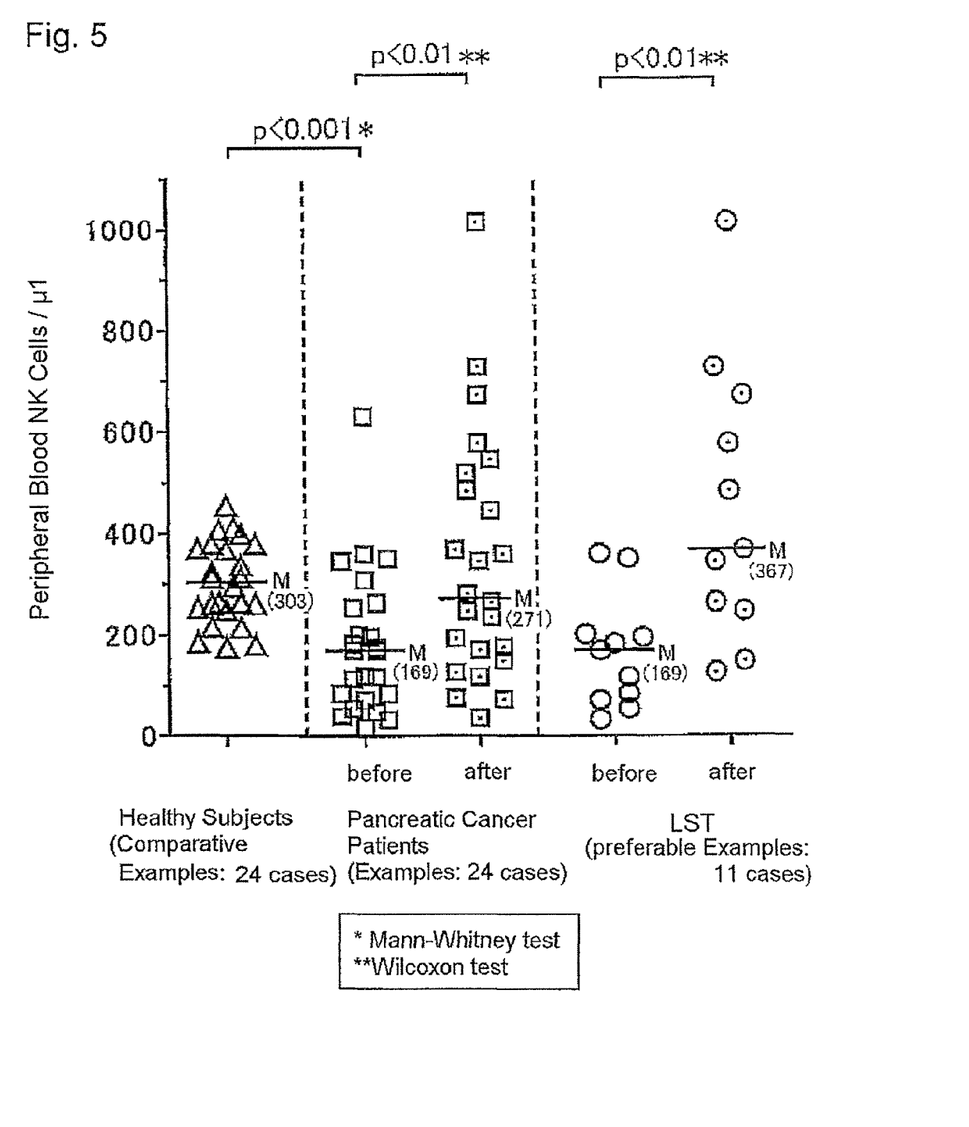
FIG. 5 is a graph plotting the numbers of NK cells in the Comparative Examples (healthy subjects) in Table 6 and in the Examples (all the pancreatic cancer patients) and preferable Examples (long-term survivors) in Table 8 in the respective columns.

FIG. 5 is a graph plotting the numbers of NK cells in the Comparative Examples (healthy subjects) in Table 6, in the Examples (all the pancreatic cancer patients), and preferable Examples (long-term survivors) in Table 8 in the respective columns.

The Examples before the initiation of the immunotherapy of the present invention exhibited lower numbers of NK cells than the Comparative Examples ($p<0.001$, by the Mann-Whitney test). Most of the Comparative Examples before the immunotherapy exhibited NK cells of 200 to 400 cells/μl, while the median value in the Examples before the immunotherapy was 169 cells/μl, or to put it another way, about 200 cells/μl. The median value obtained from these clinical data can be employed as an indicator for deciding when the immunotherapy of the present invention should be started. For example, when the number of NK cells of a patient has decreased to below 200 cells/μl, the patient will be judged to be in an immunocompromised state, so that the immunotherapy of the present invention will be started.

The number of NK cells in the Examples after the immunotherapy of the present invention increased to higher levels than that before the immunotherapy of the present invention ($p<0.01$, by the Wilcoxon test). Of the Examples after the immunotherapy, 8 cases exhibited NK cells of more than 400 cells/μl, and 5 of the 8 cases were long-term survivors. This indicates that rapid improvement and augmentation in immune function contributes to the extension of survival time.

NK Cell Cytotoxic Activity of Peripheral Blood:
The right column of Table 8 represents the NK activity before and after the immunotherapy of 22 cases in the Examples of the present invention (patients with pancreatic cancer).

Figure 6:
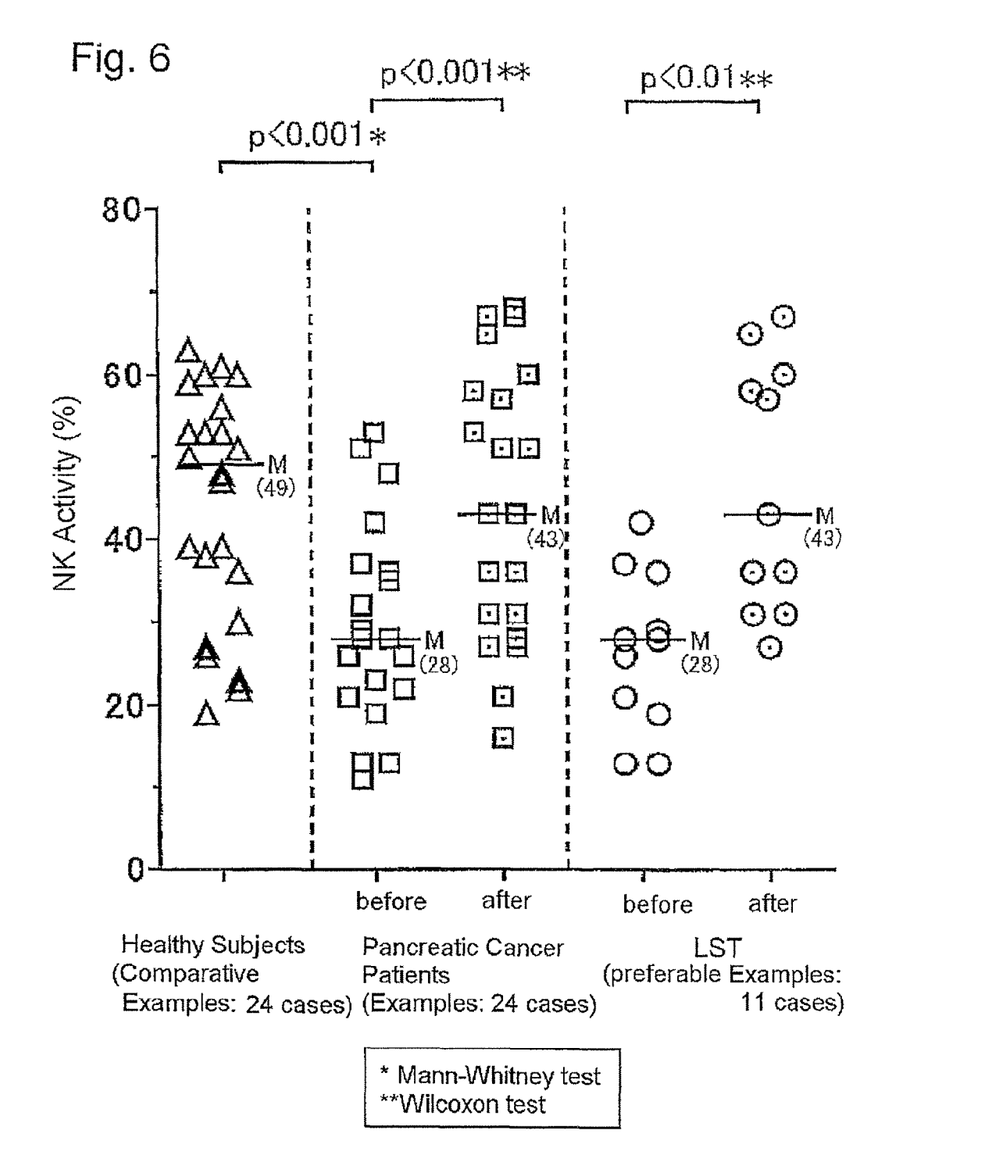
FIG. 6 is a graph plotting the NK cell cytotoxic activities in the Comparative Examples (healthy subjects) in Table 6 and in the Examples (all the pancreatic cancer patients) and preferable Examples (long-term survivors) in Table 8 in the respective columns.

FIG. 6 is a graph plotting the NK activities in the Comparative Examples (healthy subjects) in Table 6 and in the Examples (all patients with pancreatic cancer) and preferable Examples (long-term survivors) in Table 8 in the respective columns.

The Examples before the initiation of the immunotherapy of the present invention exhibited lower NK activity than the Comparative Examples ($p<0.001$, by the Mann-Whitney test). The median value in the Examples before the immunotherapy was 28%, or to put it another way, about 30%. The median value obtained from these clinical data can be employed as an indicator for deciding when the immunotherapy of the present invention should be begun. For example, when the NK activity of a patient has decreased to below 30%, the patient will be judged to be in an immunocompromised state, so that the immunotherapy of the present invention will be begun.

The NK activity in the Examples after the immunotherapy of the present invention increased to higher levels than that before the immunotherapy of the present invention ($p<0.01$, by the Wilcoxon test). The median value increased from 28% to 43%.

TABLE 8

Immunological Changes In Patients With Pancreatic Cancer Between Before And After The Immunotherapy (1)

| Examples | Peripheral Blood Lymphocytes (×10²/μl) | | NK Cells (/μl) | | NK Activity (%) | |
|---|---|---|---|---|---|---|
| | Before | After | Before | After | Before | After |
| 1* | 17 | 38 | 71 | 1015 | 13 | 67 |
| 2 | 2 | 7 | 17 | 35 | 11 | 27 |

TABLE 8-continued

Immunological Changes In Patients With Pancreatic Cancer
Between Before And After The Immunotherapy (1)

| Examples | Peripheral Blood Lymphocytes (×10²/µl) | | NK Cells (/µl) | | NK Activity (%) | |
|---|---|---|---|---|---|---|
| | Before | After | Before | After | Before | After |
| 3* | 8 | 16 | 117 | 576 | 36 | 65 |
| 4* | 10 | 20 | 169 | 726 | 42 | 57 |
| 5* | 17 | 20 | 201 | 246 | 19 | 27 |
| 6* | 18 | 28 | 349 | 483 | 28 | 36 |
| 7 | 8 | 8 | 48 | 117 | — | — |
| 8 | 14 | 16 | 175 | 193 | 26 | 16 |
| 9* | 21 | 23 | 359 | 263 | 21 | 36 |
| 10* | 2 | 7 | 33 | 127 | 28 | 31 |
| 11* | 8 | 18 | 182 | 344 | 29 | 60 |
| 12* | 8 | 18 | 54 | 149 | 13 | 43 |
| 13 | 7 | 16 | 84 | 235 | — | — |
| 14 | 9 | 16 | 344 | 358 | 23 | 51 |
| 15* | 15 | 22 | 84 | 671 | 26 | 58 |
| 16* | 14 | 37 | 195 | 367 | 37 | 31 |
| 17 | 13 | 12 | 251 | 279 | 48 | 67 |
| 18 | 9 | 11 | 40 | 73 | 13 | 21 |
| 19 | 11 | 29 | 262 | 545 | 32 | 43 |
| 20 | 22 | 22 | 306 | 170 | 22 | 28 |
| 21 | 14 | 11 | 629 | 444 | 51 | 53 |
| 22 | 10 | 22 | 169 | 517 | 28 | 51 |
| 23 | 9 | 6 | 119 | 76 | 35 | 27 |
| 24 | 7 | 12 | 113 | 175 | 53 | 68 |

*preferable Examples

Numbers of NKG2D⁺ Lymphocytes in the Peripheral Blood:

The left column of Table 9 represents the number of NKG2D⁺ lymphocytes before and after the treatments of 24 cases in the Examples of the present invention (patients with pancreatic cancer). The NKG2D⁺ lymphocytes include all of NK cells and a part of T cells.

Figure 7:
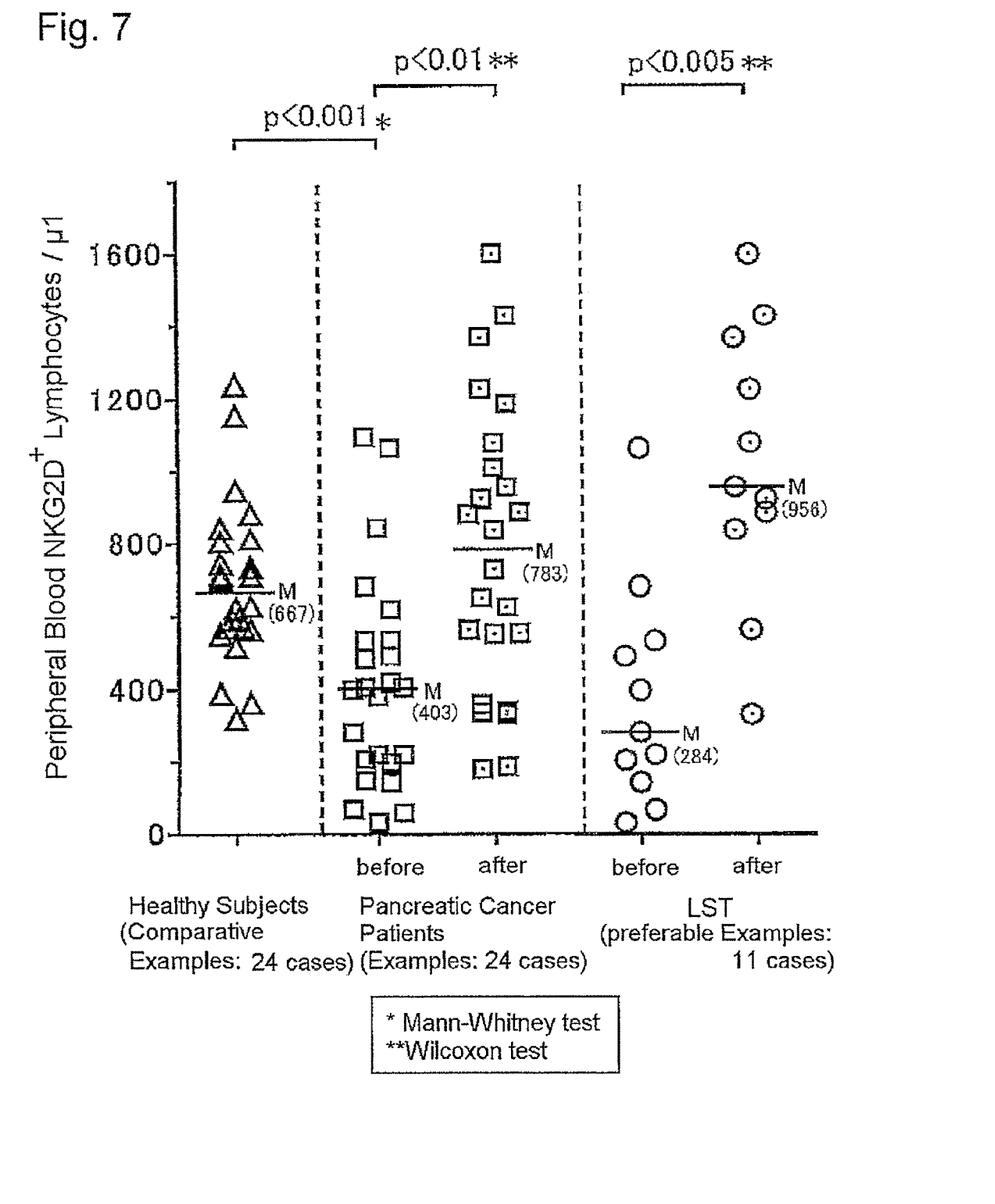
FIG. 7 is a graph in which plotting the numbers of NKG2D⁺ lymphocytes in the Comparative Examples (healthy subjects) in Table 6 and in the Examples (all the pancreatic cancer patients) and preferable Examples (long-term survivors) in Table 9 in the respective columns.

FIG. 7 is a graph plotting the numbers of NKG2D⁺ lymphocytes in the Comparative Examples (healthy subjects) in Table 6 and in the Examples (all the pancreatic cancer patients) and preferable Examples (long-term survivors) in Table 9 in the respective columns.

The Examples before the initiation of the immunotherapy of the present invention exhibited lower numbers of NKG2D⁺ lymphocytes than the Comparative Examples (p<0.001, by the Mann-Whitney test). The median value in the Examples before the immunotherapy was 403 cells/µl, or to put it another way, about 400 cells/µl. The median value obtained from these clinical data can be employed as an indicator for deciding when the immunotherapy of the present invention should be begun. For example, when the number of NKG2D⁺ lymphocytes of a patient has decreased to below 400 cells/µl, the patient will be judged to be in an immunocompromised state, so that the immunotherapy of the present invention will be begun.

The number of NKG2D⁺ lymphocytes in the Examples after the immunotherapy of the present invention increased to higher levels than that before the immunotherapy of the present invention (p<0.01, by the Wilcoxon test). The median value increased from 403 to 783 cells/µl. The increased number of NKG2D⁺ lymphocytes was due to increases not only in NK cells, but also in T cells. In the long-term survivors, it was found that the median value in the numbers of NKG2D⁺ lymphocytes was increased (nearly threefold) by the immunotherapy, and that the median value in the Examples was significantly higher than that in the Comparative Examples (p<0.01, by the Mann-Whitney test). Nine of the 11 long-term survivor exhibited NKG2D⁺ lymphocytes of 800 cells/µl or more. It was suggested that an increase in the number of NKG2D⁺ lymphocytes to 800 cells/µl or more would contribute to the extension of survival time.

CD4/CD8 ratios of peripheral blood lymphocytes:

The right column of Table 9 represents the CD4/CD8 ratios before and after the immunotherapy of 24 cases in the Examples of the present invention (patients with pancreatic cancer). Patients with cancer have a tendency to exhibit lower numbers of CD8⁺ T cells in our data, and thus smaller CD4/CD8 ratios, than healthy subjects.

Figure 8:
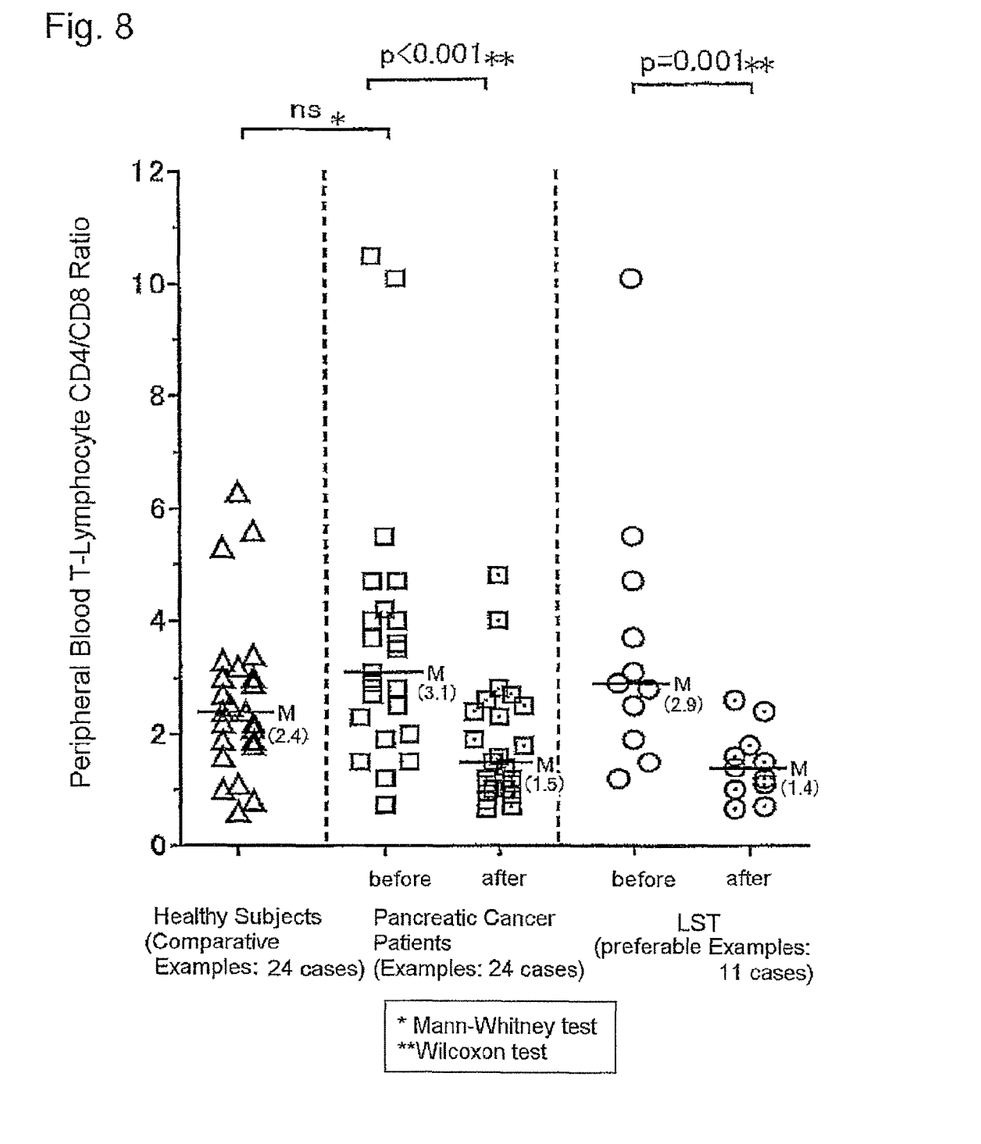
FIG. 8 is a graph plotting the CD4/CD8 ratios in the Comparative Examples (healthy subjects) in Table 6 and in the Examples (all the pancreatic cancer patients) and preferable Examples (long-term survivors) in Table 9 in the respective columns.

FIG. 8 is a graph plotting the CD4/CD8 ratios in the Comparative Examples (healthy subjects) in Table 6 and in the Examples (all the pancreatic cancer patients) and preferable Examples (long-term survivors) in Table 9 in the respective columns.

Before the initiation of the immunotherapy of the present invention, there was no statistically significant difference between the working and Comparative Examples (P>0.05, by the Mann-Whitney test). For individual cases, however, the CD4/CD8 ratios often became higher in the Examples than those in the healthy subjects. The median value in the Examples before strating the immunotherapy was 3.1, or to put it another way, about 3. When the CD4/CD8 ratio is employed as an indicator for deciding when the immunotherapy of the present invention should be begun, CD4/CD8 ratios of more than 3 will serve as a criterion.

The CD4/CD8 ratios in the Examples decreased to half after the immunotherapy of the present invention, compared to those before the immunotherapy (p<0.001, by the Wilcoxon test). The CD4/CD8 ratios in the long-term survivors also decreased to half, compared to those before the immunotherapy (p<0.0001, by the Wilcoxon test). This change is due to the increase in CD8⁺ T cells and the decrease in CD4⁺ T cells.

TABLE 9

Immunonological Changes In Patients with Pancreatic
Cancer Between Before And After The Immunotherapy (2)

| Examples | NKG2D + lymphocytes (/µl) | | CD4/CD8 | |
|---|---|---|---|---|
| | Before | After | Before | After |
| 1* | 493 | 1369 | 3.7 | 1.2 |
| 2 | 60 | 180 | | |
| 3* | 145 | 923 | 5.5 | 1.5 |
| 4* | 399 | 1230 | 2.8 | 1.4 |
| 5* | 683 | 886 | 1.9 | 1.8 |
| 6* | 32 | 1430 | 2.5 | 0.7 |
| 7 | 198 | 555 | 4.0 | 2.8 |
| 8 | 619 | 187 | 10.5 | 2.5 |
| 9* | 1064 | 956 | 1.2 | 1.0 |
| 10* | 69 | 333 | 3.1 | 1.6 |
| 11* | 284 | 564 | 4.7 | 2.6 |
| 12* | 221 | 838 | 2.9 | 1.1 |
| 13 | 149 | 651 | 3.5 | 1.9 |
| 14 | 536 | 728 | 1.5 | 1.0 |
| 15* | 206 | 1080 | 10.1 | 2.4 |
| 16* | 535 | 1600 | 1.5 | 0.7 |
| 17 | 407 | 338 | 4.0 | 4.8 |
| 18 | 221 | 553 | 2.7 | 1.1 |
| 19 | 484 | 1010 | 4.2 | 2.3 |
| 20 | 1096 | 881 | 2.0 | 0.9 |
| 21 | 844 | 625 | 3.6 | 2.7 |
| 22 | 407 | 1188 | 2.3 | 0.8 |
| 23 | 419 | 360 | 0.7 | 1.2 |
| 24 | 381 | 341 | 4.7 | 4.0 |

*preferable Examples

What is claimed is:

1. An immunotherapy for pancreatic cancer, which comprises the steps of: culturing peripheral blood lymphocytes of a patient with pancreatic cancer by stimulating the lymphocytes with an anti-CD3 antibody and an anti-CD52 antibody, thereby to obtain an immunotherapeutic agent, and administering at least four infusions of the immunotherapeutic agent to the same patient, wherein each of the infusions of the immunotherapeutic agent comprise at least $15 \times 10^9$ cells of activated lymphocytes, the percentage of $CD3^- CD56^+$ NK cells in the activated lymphocytes is at least 30%, and the administration of the immunotherapeutic agent is begun for the patients with pancreatic cancer who fulfill at least one of the following immunocompromised states:

(a) the number of peripheral blood lymphocytes being less than 1,000 cells/μl;

(b) the number of $CD3^- CD56^+$ NK cells in the peripheral blood lymphocytes being less than 200 cells/μl;

(c) the cytotoxic activity of $CD3^- CD56^+$ NK cells in the peripheral blood being less than 30%; and (d) the number of $NKG2D^+$ lymphocytes in the peripheral blood being less than 400 cells/μl.

2. The immunotherapy for pancreatic cancer according to claim 1, wherein the immunotherapeutic agent is administered to the patient with pancreatic cancer having a CD4/CD8 ratio of more than 3 in the peripheral blood.

3. The immunotherapy for pancreatic cancer according to claim 1, wherein the administered activated lymphocytes except for NK cells are either or both of $CD4^+$ T cells and $CD8^+$ T cells.

4. The immunotherapy for pancreatic cancer according to claim 1, wherein the immunotherapeutic agent is administered in combination with anti-cancer agents.

* * * * *